United States Patent [19]
McGeorge

[11] Patent Number: 6,010,466
[45] Date of Patent: Jan. 4, 2000

[54] SUCTION NIPPLE EVERSION DEVICE AND METHOD OF USE

[76] Inventor: Douglas Donald McGeorge, Redmarley Cavendish Road, Chester Chesire, United Kingdom, CH4 8JN

[21] Appl. No.: 08/244,118

[22] PCT Filed: Nov. 20, 1992

[86] PCT No.: PCT/GB92/02159

§ 371 Date: May 19, 1994

§ 102(e) Date: May 19, 1994

[87] PCT Pub. No.: WO93/11806

PCT Pub. Date: Jun. 24, 1993

[30] Foreign Application Priority Data

Dec. 10, 1991 [GB] United Kingdom .................... 9126230

[51] Int. Cl.[7] .................................................. A61N 1/00
[52] U.S. Cl. .................................................. 601/14; 601/6
[58] Field of Search ............................................ 601/6–14

[56] References Cited

U.S. PATENT DOCUMENTS

| | | | |
|---|---|---|---|
| 196,594 | 10/1877 | Patch | 128/890 |
| 727,464 | 5/1903 | Scott | 601/14 |
| 1,032,518 | 7/1912 | Thieringer | 128/890 |
| 1,212,845 | 1/1917 | Talley | 601/6 |
| 1,472,234 | 10/1923 | Thomas | 601/14 |
| 1,922,947 | 8/1933 | Grotte | 601/14 |
| 3,785,369 | 1/1974 | Tallent | 601/14 |
| 4,111,192 | 9/1978 | Wu | 601/14 |
| 5,032,103 | 7/1991 | Larsson | 128/890 X |

FOREIGN PATENT DOCUMENTS

| | | | |
|---|---|---|---|
| A-56110/86 | 10/1986 | Australia . | |
| 1261655 | 10/1986 | U.S.S.R. | 601/14 |
| 2995 | 2/1911 | United Kingdom | 601/14 |
| 2240924 | 8/1991 | United Kingdom | 601/14 |

*Primary Examiner*—Robert A. Hafer
*Assistant Examiner*—Brian E. Hanlon

[57] ABSTRACT

A device incorporating a transparent nipple mold (1) with a sealing flange (2) attached to a valve and syringe port (3). With the device held on the breast, over the nipple areolar complex, air can be withdrawn and the inverted nipple sucked up into the mold (1). Periodic use stretches up the short lactiferous ducts.

11 Claims, 1 Drawing Sheet

SUCTION NIPPLE EVERSION DEVICE AND METHOD OF USE

BACKGROUND OF THE INVENTION

The present invention relates to a suction nipple eversion device for the correction of inverted nipples.

Inverted nipples are a common problem caused by short lactiferous ducts. Many operative procedures are available for their correction but all have limitations.

SUMMARY OF THE INVENTION

It is therefore an object of the present invention to provide a simple device for correcting inverted nipples which obviates the need for operative intervention.

Accordingly, the present invention resides in a suction nipple eversion device comprising a nipple mould for receiving a nipple, the nipple mould being provided with a valve by means of which air can be withdrawn from the nipple mould and a sealing flange for sealing the nipple mould against a nipple areolar complex of the breast under negative pressure produced upon withdrawal of air and wherein in use the device is self-supporting.

In use, the device according to the present invention operates by producing a suction effect on the inverted nipple, the negative pressure acting to draw out the inverted nipple into the mould. Since the device supports itself, individuals are free to move about during use. The device is worn for intervals over a period of time resulting in stretching of the lactiferous ducts and thereby providing a simple means for the correction of inverted nipples.

Preferably, the valve is provided with a syringe port and is attached to the nipple mould by means of a flexible tube. When the device is held against the nipple areolar complex of the breast air can be withdrawn through the valve by means of a syringe.

The nipple may be visualised during use through a transparent mould.

Removal is effected by simply lifting the device off the breast from the edge of the sealing flange so disrupting the seal and equalising the pressure.

BRIEF DESCRIPTION OF THE DRAWINGS

The invention will now be described by way of example with reference to the accompanying drawings in which.

DETAILED DESCRIPTION OF THE PREFERRED EMBODIMENTS

Figure 1:
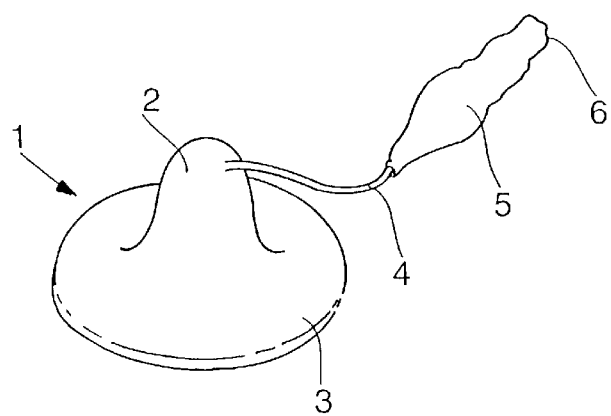
FIG. 1 is a perspective view of a suction nipple eversion device.

FIG. 1 shows a suction nipple eversion device 1 comprising a nipple mould 2 provided with a sealing flange 3 and a nipple reciving portion 8, including a sidewall 9 and a top portion 10. The mould 2 is provided with a valve 4 connected to the mould by means of a flexible tube 5. The valve 4 (details of which are not shown) has a syringe port 6 for receiving a syringe to extract air from the mould.

Figure 3:
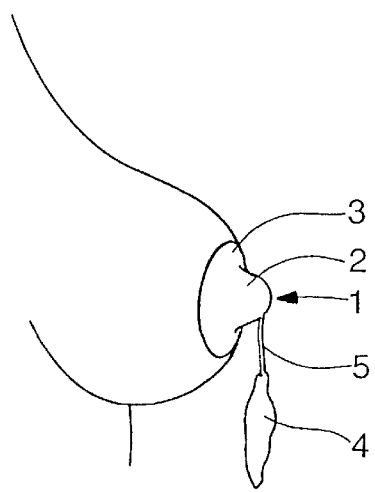
FIG. 3 is a perspective view of a suction nipple eversion device in use.
Figure 2:
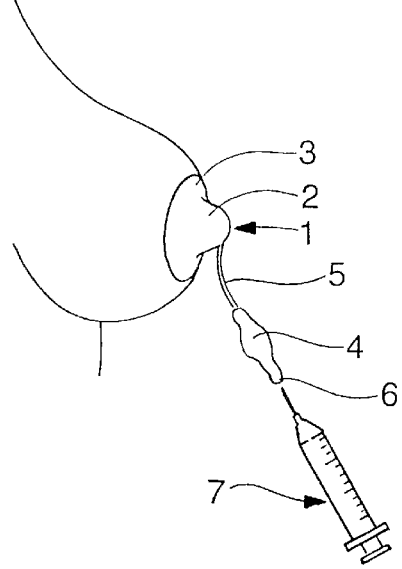
FIG. 2 is a perspective view showing a syringe being used to extract air from the nipple mould of a suction nipple eversion device.

In FIG. 2 there is shown the suction nipple eversion device 1 of FIG. 1 held against a patient's breast. A syringe 7 is introduced into the device via the syringe port 6 whereupon valve 4 (details not shown) opens to allow withdrawal of air by the syringe 7. Once suction has been achieved the syringe 7 is withdrawn whereupon valve 4 closes to allow the mould to be retained in position over the nipple areolar complex as shown in FIG. 3.

Figure 4:
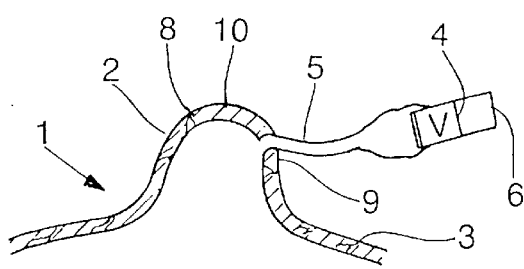
FIG. 4 is a cross-sectional view of the device of FIGS. 1 to 3.

A cross-section of the device 1 is shown at FIG. 4.

It will be appreciated by those skilled in the art that various types of valves may be utilized with the present invention without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A suction nipple eversion device comprising:
   a nipple mould for receiving a nipple of a breast of a user of the device, the nipple mould including
   (i) a side wall,
   (ii) a closed top wall;
   (iii) an open bottom through which the nipple is introduced into the nipple mould;
   (iv) a sealing flange extending from the side wall adjacent the bottom for sealing the nipple mould against a nipple areolar complex of the breast under negative pressure produced upon withdrawal of air from the nipple mould; and
   (v) an aperture in the nipple mould;
   (b) a valve;
   (c) a flexible tube extending between the aperture and the valve to allow fluid communication between the nipple mould and the valve; and
   (d) a vacuum source removably attached to the valve;
   whereby in use air is withdrawn from the nipple mould through the flexible tube by the vacuum source to create suction, the vacuum source is removed and suction is maintained in the nipple mould by the valve, and the device is capable of being self-supporting upon the nipple areolar complex for a time period to stretch lactiferous ducts in the breast to thereby correct the inverted nipple.

2. A suction nipple eversion device according to claim 1 wherein the flexible tube projects laterally from the side wall.

3. A suction nipple eversion device according to claim 1 wherein the nipple mould is a one piece construction.

4. A suction nipple eversion device according to claim 1 wherein the valve comprises a syringe port.

5. A suction nipple eversion device according to claim 1 wherein the nipple mould is transparent.

6. A method for correcting an inverted nipple of a breast of a person comprising
   (a) sealing a nipple mould of a suction nipple eversion device to a nipple areolar complex of the breast by withdrawing air between the nipple mould and the nipple areolar complex with a vacuum source removably connected to a valve in fluid communication with the nipple mould; the suction nipple eversion device comprising said nipple mould for receiving the nipple and said valve in fluid communication with the nipple mould to allow the withdrawal of air from the nipple mould, the nipple mould including a sealing flange for sealing the nipple mould against the nipple areolar complex of the breast under negative pressure produced upon the withdrawal of air, whereby the device in use is self-supporting upon the nipple areolar complex;

(b) disconnecting the vacuum source from the nipple mould while maintaining a vacuum between the nipple mould and the nipple areolar complex; and (c) stretching lactiferous ducts in the breast by maintaining the self-supporting suction nipple eversion device in sealing engagement with the nipple areolar complex for intervals over a period of time to thereby correct the nipple inversion.

7. A method according to claim 6 wherein said vacuum source is a syringe.

8. A method according to claim 6 wherein the nipple mould is a one piece construction.

9. A method according to claim 6 wherein the nipple mould is transparent.

10. A method according to claim 6 wherein the nipple mould includes a side wall, a closed top wall, an open bottom through which the nipple is introduced into the nipple mould, and an aperture in the side wall through which the valve and the nipple mould communicate.

11. A method according to claim 10 wherein the suction nipple eversion device includes a flexible tube extending between the side wall aperture and the valve to allow fluid communication between valve and the nipple mould.

* * * * *